(12) United States Patent
Seeney et al.

(10) Patent No.: US 8,651,113 B2
(45) Date of Patent: Feb. 18, 2014

(54) MAGNETICALLY RESPONSIVE NANOPARTICLE THERAPEUTIC CONSTRUCTS AND METHODS OF MAKING AND USING

(75) Inventors: Charles E. Seeney, Edmond, OK (US); Jim Klostergaard, Kingwood, TX (US); William A. Yuill, Edmond, OK (US); Donald D. Gibson, Edmond, OK (US)

(73) Assignee: SWR&D Inc., Lawton, OK (US)

( * ) Notice: Subject to any disclaimer, the term of this patent is extended or adjusted under 35 U.S.C. 154(b) by 969 days.

(21) Appl. No.: 12/505,111

(22) Filed: Jul. 17, 2009

(65) Prior Publication Data

US 2011/0130616 A1    Jun. 2, 2011

Related U.S. Application Data

(63) Continuation-in-part of application No. 11/400,620, filed on Apr. 6, 2006, now Pat. No. 8,001,977, and a continuation-in-part of application No. 10/871,243, filed on Jun. 18, 2004, now Pat. No. 7,723,311, and a continuation-in-part of application No. 11/712,112, filed on Feb. 28, 2007, now abandoned, which is a continuation-in-part of application No. 10/965,056, filed on Oct. 14, 2004, now Pat. No. 7,344,491, which is a continuation-in-part of application No. 10/724,563, filed on Nov. 26, 2003, now abandoned.

(60) Provisional application No. 60/669,681, filed on Apr. 8, 2005, provisional application No. 60/479,381, filed on Jun. 18, 2003.

(51) Int. Cl.
*A61B 19/00*    (2006.01)

(52) U.S. Cl.
USPC ........................................... 128/899

(58) Field of Classification Search
USPC ................. 128/897–899; 600/9–15
See application file for complete search history.

(56) References Cited

U.S. PATENT DOCUMENTS 3,905,841 A    9/1975  Simonetti
(Continued)

FOREIGN PATENT DOCUMENTS

DE    4309333    9/1994
(Continued)

OTHER PUBLICATIONS

Massart; "Preparation of Aqueous Magnetic Liquids in Alkaline and Acidic Media"; IEEE Transactions on Magnetics; Mar. 1981; vol. Mag-17; No. 2, pp. 1247-1248.
(Continued)

*Primary Examiner* — Charles A Marmor, II
*Assistant Examiner* — Catherine E Burk
(74) *Attorney, Agent, or Firm* — Tomlinson Rust McKinstry Grable

(57) ABSTRACT

Magnetically responsive therapeutic carriers comprise nanoparticles including single-domain nanoparticles comprising magnetite and having an average particle size ranging between 1 and 50 nanometers, clusters of the single-domain nanoparticles, the clusters having an average cluster size ranging between 5 and 1000 nanometers, and mixtures of the two. The single-domain nanoparticles are encapsulated with a silica coating. A silane coupling agent is bonded to the silica coating and has a specific pendant functional group capable of selectively binding with the therapeutic. Preferably, the bond between the specific pendant functional group and the therapeutic is a covalent bond. The movement of magnetically responsive nanoparticle therapeutic constructs, with concentration and extravasation/endocytosis at a target site, such as cancerous tumors, uses a controllable magnetic field generator adapted to move the therapeutic constructs in three dimensions, and is enhanced using a repetitively-varying magnetic field. A method for treating cancer comprises administering and magnetically guiding a therapeutic construct comprising paclitaxel.

23 Claims, 6 Drawing Sheets
(2 of 6 Drawing Sheet(s) Filed in Color)

(56) References Cited

U.S. PATENT DOCUMENTS

| | | | |
|---|---|---|---|
| 4,336,546 A | 6/1982 | Edwards et al. | |
| 4,356,029 A | 10/1982 | Down et al. | |
| 4,376,740 A | 3/1983 | Uda et al. | |
| 4,466,896 A | 8/1984 | Darden | |
| 4,501,726 A | 2/1985 | Schroder et al. | |
| 4,526,922 A | 7/1985 | Pickwell et al. | |
| 4,652,257 A | 3/1987 | Chang | |
| 4,687,511 A | 8/1987 | Paliwal et al. | |
| 4,690,130 A | 9/1987 | Mirell | |
| 5,061,586 A | 10/1991 | Saha et al. | |
| 5,069,936 A | 12/1991 | Yen | |
| 5,069,971 A | 12/1991 | Waketa et al. | |
| 5,160,725 A | 11/1992 | Pilgrimm | |
| 5,349,957 A | 9/1994 | Yudelson | |
| 5,427,767 A | 6/1995 | Kresse et al. | |
| 5,512,474 A | 4/1996 | Clapper et al. | |
| 5,549,915 A | 8/1996 | Volonsky et al. | |
| 5,578,325 A | 11/1996 | Domb et al. | |
| 5,651,989 A | 7/1997 | Volonsky et al. | |
| 5,695,901 A | 12/1997 | Selim | |
| 5,705,195 A | 1/1998 | Volonsky et al. | |
| 5,711,803 A | 1/1998 | Pehnt et al. | |
| 5,753,477 A | 5/1998 | Chan | |
| 5,788,738 A | 8/1998 | Pirzada et al. | |
| 5,851,507 A | 12/1998 | Pirzada et al. | |
| 5,876,683 A | 3/1999 | Glumac et al. | |
| 5,916,539 A * | 6/1999 | Pilgrimm | 424/9.322 |
| 5,928,958 A | 7/1999 | Pilgrimm | |
| 5,976,824 A | 11/1999 | Gordon | |
| 5,984,997 A | 11/1999 | Bickmore et al. | |
| 5,992,641 A | 11/1999 | Caldwell | |
| 6,004,786 A | 12/1999 | Yamashita et al. | |
| 6,007,845 A | 12/1999 | Domb et al. | |
| 6,014,580 A | 1/2000 | Blume et al. | |
| 6,020,507 A * | 2/2000 | Gibson | 549/510 |
| 6,048,515 A | 4/2000 | Kresse et al. | |
| 6,123,920 A | 9/2000 | Gunther et al. | |
| 6,153,172 A | 11/2000 | Schroder | |
| 6,187,259 B1 | 2/2001 | Yamashita et al. | |
| 6,200,547 B1 | 3/2001 | Volkonsdy et al. | |
| 6,203,777 B1 | 3/2001 | Schroder | |
| 6,207,195 B1 | 3/2001 | Walsh et al. | |
| 6,254,940 B1 | 7/2001 | Pratsinis et al. | |
| 6,255,477 B1 | 7/2001 | Kleiber et al. | |
| 6,274,121 B1 | 8/2001 | Pilgrimm | |
| 6,274,554 B1 | 8/2001 | Magal et al. | |
| 6,284,282 B1 | 9/2001 | Maa et al. | |
| 6,344,357 B1 | 2/2002 | Rickwood | |
| 6,409,925 B1 | 6/2002 | Gombinsky et al. | |
| 6,436,028 B1 | 8/2002 | Dormer | |
| RE37,853 E | 9/2002 | Detering et al. | |
| 6,472,632 B1 | 10/2002 | Peterson et al. | |
| 6,482,436 B1 | 11/2002 | Volkonsky et al. | |
| 6,514,481 B1 | 2/2003 | Prasad et al. | |
| 6,548,264 B1 | 4/2003 | Tan et al. | |
| 6,580,051 B2 | 6/2003 | Peterson et al. | |
| 6,602,543 B2 | 8/2003 | Yadav et al. | |
| 6,620,627 B1 | 9/2003 | Libertii et al. | |
| 6,623,982 B1 | 9/2003 | Liberti et al. | |
| 6,739,342 B1 * | 5/2004 | Fredriksson et al. | 128/899 |
| 6,763,607 B2 | 7/2004 | Beyerinck et al. | |
| 6,767,635 B1 | 7/2004 | Bahr et al. | |
| 6,767,637 B2 | 7/2004 | Park et al. | |
| 6,884,817 B2 | 4/2005 | Li et al. | |
| 6,962,685 B2 | 11/2005 | Sun | |
| 7,169,348 B2 | 1/2007 | Zhu et al. | |
| 7,169,618 B2 | 1/2007 | Skold | |
| 7,189,198 B2 | 3/2007 | Harburn et al. | |
| 7,344,491 B1 | 3/2008 | Seeney et al. | |
| 7,465,579 B2 | 12/2008 | Hatakeyama et al. | |
| 2001/0039919 A1 | 11/2001 | Hunt et al. | |
| 2002/0046993 A1 | 4/2002 | Peterson et al. | |
| 2002/0053557 A1 | 5/2002 | Peterson et al. | |
| 2002/0086842 A1 | 7/2002 | Plank et al. | |
| 2002/0098529 A1 * | 7/2002 | Tan et al. | 435/7.21 |
| 2002/0147424 A1 | 10/2002 | Ostrow et al. | |
| 2002/0155059 A1 | 10/2002 | Boulos et al. | |
| 2002/0160190 A1 | 10/2002 | Yadav et al. | |
| 2003/0201208 A1 * | 10/2003 | Koch et al. | 209/39 |
| 2003/0215394 A1 | 11/2003 | Short et al. | |
| 2004/0133099 A1 | 7/2004 | Dyer, Jr. et al. | |
| 2004/0210289 A1 * | 10/2004 | Wang et al. | 607/116 |
| 2004/0242631 A1 * | 12/2004 | Garlich et al. | 514/312 |
| 2005/0271732 A1 | 12/2005 | Seeney et al. | |
| 2007/0041901 A1 | 2/2007 | Diener et al. | |
| 2007/0196281 A1 | 8/2007 | Jin et al. | |
| 2007/0231908 A1 | 10/2007 | Cai et al. | |
| 2008/0038191 A1 * | 2/2008 | Perrin et al. | 424/1.45 |

FOREIGN PATENT DOCUMENTS

| | | |
|---|---|---|
| WO | 9801160 | 1/1998 |
| WO | 9960998 | 12/1999 |
| WO | 0117611 | 3/2001 |
| WO | 02056890 A1 | 7/2002 |
| WO | 03059194 A2 | 7/2003 |
| WO | 2004006765 | 1/2004 |

OTHER PUBLICATIONS

Chang; "Adriamycin-Loaded Immunological Magnetic Nanoparticles: Site-Specific Targeting . . . "; Chinese Journal of Biomedical Eng.; 1996; vol. 15, No. 4, pp. 354-359.

Moskowitz; "Domain Theory"; Hitchhiker's Guide to Magnetism, Environmental Magnetism Workshop; Jun. 1991; pp. 21-33.

"Training Papers Spray Drying"; Buchi Labortechnick AG; 1997-2002; English Version B; pp. 1-19.

Correa-Duarte et al.; Control of Packing Order of Self-Assembled Monolayers of Magnetite Nanoparticles with and without SiO2 . . . ; Langmuir; 1998; vol. 14; pp. 6430-6435.

Shutt et al.; "Biocompatible Magnetic Polymer Carriers for In Vitro Radionuclide Delivery"; Int. Soc. For Artificial Organs; 1999; vol. 23; No. 1; pp. 98-103.

Utreja et al.; "Lipoprotein-Mimicking Viovectorized Systems for Methotraxate Delivery"; Pharmaceutica Acta Helvetia; 1999; pp. 275-279 (Abstract XP-002383903).

Alexiou et al.; "Locoregional Cancer Treatment with Magnetic Drug Targeting"; Cancer Research; Dec. 1, 2000; vol. 60; pp. 6641-6648.

Caruso et al.; Chem. Mater.; 13:109-116; 2001.

Nicoli et al.; "Design of Triptorelin Loaded Nanospheres for Transdermal Iontophoretic Administration"; Int. Journal of Pharmaceutics; 2001; No. 214; pp. 31-35.

Zhang et al.; "Surface Modification of Superparamagnetic Magnetite Nanoparticles . . "; Dept. of Materials Science & Engineering; Aug. 8, 2001; pp. 1553-1561.

Bioeletromagnetics Society (BEMS) "Magnets Help Target Gene Therapy"; Press Release; 2002.

Barbric; "Single Domain Magnets in Bio-Medical Applications"; European Cells and Materials; 2002; vol. 3; Suppl. 2; pp. 132-134.

Brigger et al.; "Nanoparticles in Cancer Therapy and Diagnosis"; Advanced Drug Delivery Reviews; 2002; vol. 54; pp. 631-651.

Duclairor et al.; "Alpha-Tocopherol Encapsulation and In Vitro Release from Wheat Gliadin Nanoparticles"; J. Microencapsulation; 2002; vol. 19; No. 1; pp. 53-60.

Johnson et al.; "The MTC Technology: A Platform Technology for the Site-Specific Delivery of Pharmaceutical Agents"; European Cells and Materials; 2002; vol. 3, Suppl. 2; pp. 12-15.

Mornet et al.; "Maghemite@silica Nanoparticles for Biological Applications"; European Cells and Materials; 2002; vol. 3; Suppl. 2; pp. 110-113.

Panyam et al.; "Rapid Endo-Lysomal Escape of Poly(DL-lactide-co-glycolide) Nanoparticles . . . "; Dept. Pharm. Sci.; Apr. 18, 2002; vol. 17; pp. 1217-1226.

Prabha et al.; Size-Dependency of Nanoparticle-Mediated Gene Transfection . . . ; Int. J. Pharm.; Jun. 6, 2002; vol. 224; pp. 105-115.

Lackey et al.; "A Biomimetic pH-Responsive Polymer Directs Endosomal Release . . . ", Bio. Chem.; Jul. 25, 2002; vol. 13; No. 5; pp. 996-1001.

(56) References Cited

OTHER PUBLICATIONS

Wilhelm et al.; "Intracellular Uptake of Anionic Superparamagnetic Nanoparticles . . . "; Biomaterials; Sep. 9, 2002; vol. 24; pp. 1001-1011.

Panyam et al.; "Biodegradable Nanoparticles for Drug and Gene . . . "; Dept. Pharm. Sciences; Sep. 16, 2002; pp. 329-347.

"Nanoparticle News"; Business Communications Company (electronic publication); Oct. 2002.

Bringley et al.; "Controlled Chemical and Drug Delivery . . . "; J. Dispersion Science and Tech; 2003; vol. 24; Nos. 3 and 4; pp. 589-605.

Jones et al.; "Poly(2-alkyacrylic acid) Polymers Deliver Molecules to . . . Endosomal Vesicles"; Biochem. J.; 2003; vol. 372; pp. 65-75.

Murthy et al.; "Bioinspired pH-Responsive Polymers for . . . "; Dept. of Bioengineering and Dept. of Pathology; Jan. 15, 2003; vol. 14; pp. 412-419.

Suh et al.; "Efficient Active Transport of Gene Nanocarriers"; Dept. of Biomed Eng . . . , Mol. Biophysics Prog., John Hopkins Univ., Baltimore, MD; Apr. 1, 2003.

Plank et al.; "The Magnetoflection Method: Using Magnetic Force to Enhance Gene Delivery"; Biol. Chem.; May 2003; vol. 384; pp. 737-747.

Liu et al.; "Nanoparticles of Compacted DNA Transfect Postmitotic Cells"; Journal of Biological Chemistry; Jun. 14, 2003; vol. 278; No. 35; pp. 32578-32586.

Berry et al.; "Functionalisation of Magnetic Nanoparticles . . . "; J. Physics D: Applied Physics; Jun. 18, 2003; pp. R198-R206.

Pankhurst et al.; "Applications of Magnetic Nanoparticles in Biomedicine"; Journal of Physics D: Applied Physics; Jun. 18, 2003; pp. R167-R1181.

Tartaj et al.; "The Preparation of Magnetic Nanoparticles for Applications in Biomedicine"; Journal of Physics; Jun. 18, 2003; pp. R182-R197.

He et al.; "A Novel Method . . . Amino-Modified Silica Coated Magnetic Nanoparticles"; Rev. Adv. Mater. Sci.; Jul. 27, 2003; vol. 5; pp. 375-380.

Goyya et al.; "Static and Dynamic Magnetic Properties of Spherical Magnetite Nanoparticles"; J. Applied Physics; vol. 94; No. 5; Sep. 1, 2003; pp. 3520-3528.

Mondalek; "Concerns Regarding the . . . Attached to a Drug/Gene"; OU Health Sciences Center Oklahoma City, Oklahoma; Article for Review; Oct. 28, 2003.

Farokhzad et al.; "Nanoparticle-Aptamer Bioconjugates, A New Approach for Targeting . . . "; Cancer Research; Nov. 1, 2004; vol. 64; pp. 7668-7672.

Miller et al., "Why Use Remote Guidance to Steer Catheters and Guard Wires?"; Radiology; Aug. 2004; pp. 313-314; vol. 232, No. 2.

"The Basics of Silane Chemistry"; A Guide to Silane Solutions from Dow Corning; Dow Corning Corporation; 2005; pp. 7-85.

PCT Written Opinion; PCT/US2004/027225 May 23, 2005, 6 pages.

Mason; "Targeted Drug Delivery Achieved with Nanoparticle-Aptamer Bioconjugates"; Medical News Today; Nov. 6, 2005; available at www.medicalnewstoday.com.

Jurgons, et al.; "Drug Loaded Magnetic Nanoparticles for Cancer Therapy"; J. Phys.: Condens. Matter; 2006; vol. 18, pp. S2893-S2902.

Thorek et al., "Superparamagnetic Iron Oxide Nanoparticle Probes for Molecular Imaging"; Cellular and Molecular Imaging Group, Department of Bioengineering, University of Pennsylvania; 2006; 17 pages.

Thornton et al.; "Magnetic Assisted Navigation in Electrophysiology and Cardiac Resynchronisation: A Review"; Indian Pacing and Electrophys. J.; 2006; vol. 6; No. 4; pp. 202-213.

"Domain University Theory"; author unknown; available from Institute for Rock Magnetism, University of Minnesota, at www.irm.edu/hg2m/hg2m_d/hg2m-d.html, last visited Jul. 2007.

Klostergaard et al.; "Magnetic Vectoring of Magnetically . . . within the Murine Peritoneum"; J. of Magnetism and Magnetic Materials; Apr. 2007; vol. 311; pp. 330-335.

"Small Interfering RNA"; Wikipedia webpage; printed Apr. 2008; 6 pages.

\* cited by examiner

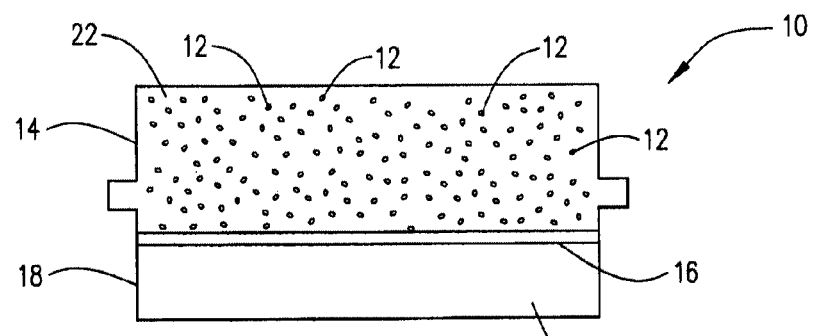
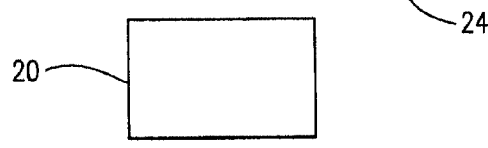
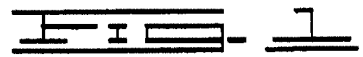
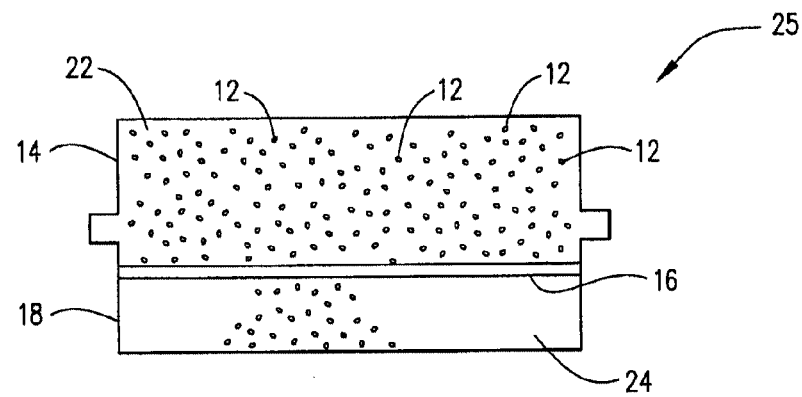
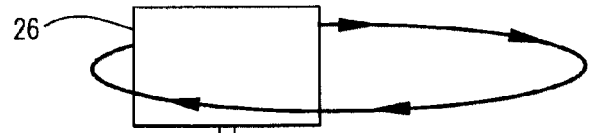
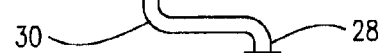
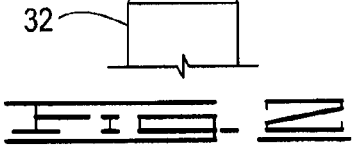

Pos 1.94 mm R
060418-0E: 2
D06-T2FSE-Sag, 6:1
Pos -0.68 mm L
060418-0E-2hr: 5
D06-T2FSE-Sag, 6:1
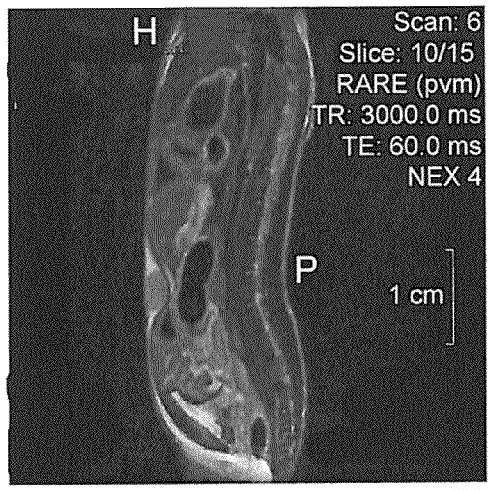 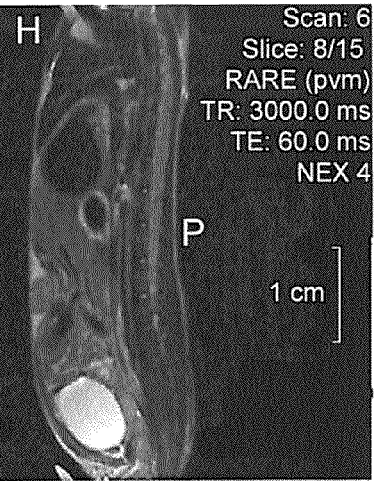
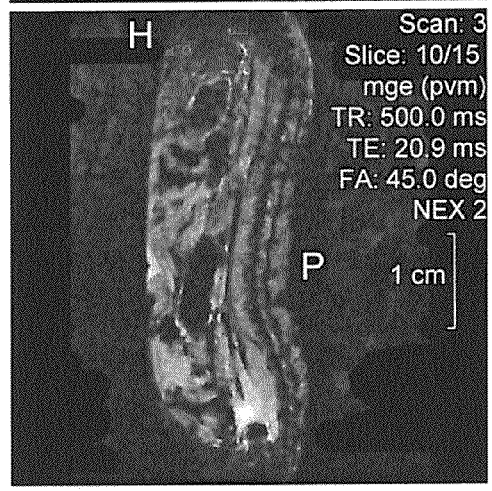 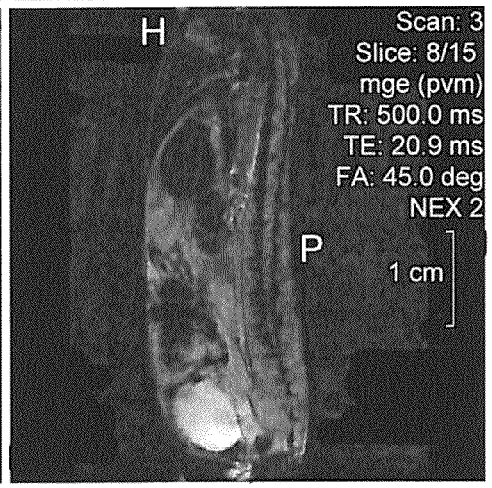
Pos 1.94 mm R
060418-0E: 2
D03-T2Star-Sag, 3:1
Pos -0.68 mm L
060418-0E-2hr: 5
D03-T2Star-Sag, 3:1
Mouse F 5.0 kg
SI 1.00/1.25 mm
FOV 5.0/3.8 cm
FIG. 6

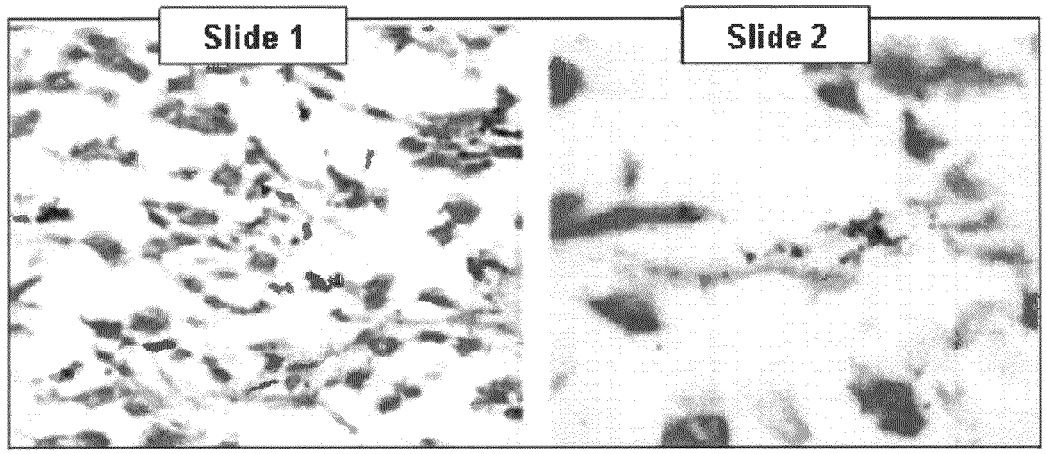

H & E-stained sections of HEY tumors from mice subjected to i.v. administration of Si-MNPs, with tandem magnet juxtaposed over the tumor during MNP injection and for 2 hr thereafter. Viewed at up to 100X under oil immersion. Note presence of apparent MNP aggregates as well as a few possible individual MNPs. Some MNPs are seen to overlay the HEY cells, but may or may not be internalized. No MNPs were detected in control tumors from non-magnetically vectored mice that received i.v. MNPs.

FIG. 7

MAGNETICALLY RESPONSIVE NANOPARTICLE THERAPEUTIC CONSTRUCTS AND METHODS OF MAKING AND USING

CROSS REFERENCE TO RELATED APPLICATIONS

This application is a continuation-in-part of U.S. patent application Ser. No. 11/400,620 filed Apr. 6, 2006 now U.S. Pat. No. 8,001,977, which claims priority to U.S. Provisional Patent Application Ser. No. 60/669,681 filed Apr. 8, 2005; a continuation-in-part of U.S. patent application Ser. No. 10/871,243 filed Jun. 18, 2004 now U.S. Pat. No. 7,723,311; and a continuation-in-part of U.S. patent application Ser. No. 11/712,112 filed Feb. 28, 2007 now abandoned, which was a continuation-in-part of U.S. patent application Ser. No. 10/965,056 filed Oct. 14, 2004, now U.S. Pat. No. 7,344,491, which was a continuation-in-part of U.S. patent application Ser. No. 10/724,563 filed Nov. 26, 2003, now abandoned, and which claimed priority to U.S. Provisional Patent Application Ser. No. 60/479,381 filed Jun. 18, 2003; and wherein the contents of each are hereby expressly incorporated by reference herein in their entirety.

STATEMENT REGARDING FEDERALLY SPONSORED RESEARCH OR DEVELOPMENT

This invention was partially funded by the Government under grants from the Department of Defense Breast Cancer Research Program and the Alliance for Nanohealth, which is also funded by the Department of Defense. The Government has certain rights to portions of the invention.

BACKGROUND

1. Field of Invention

The present invention relates generally to magnetically responsive nanoparticle therapeutic carriers, and more particularly, but not by way of limitation, to nanoparticle therapeutic carrier and construct compositions, methods of making magnetically responsive nanoparticle therapeutic constructs, and methods of delivering such constructs to target cells within a body.

2. Background of the Invention

Nanoparticles generally refer to particles having at least one dimension of about 100 nanometers or less. Magnetic nanoparticles offer many potentially enhanced medical treatment options due to their very small size and the ability to manipulate their movement using an externally applied magnetic field gradient. A major goal in medical applications using magnetic nanoparticle carriers is to increase deposition in a specific target area so as to increase the dose in the affected area and to allow less dosage in non-affected areas. For example, the particles may be used as carriers for pharmaceuticals, such as anticancer drugs, and the carrier particles may be magnetically targeted to a specific area of the body, such as a tumor.

In many applications of this technology, what is needed is improved chemical bonding of the therapeutic to the magnetic nanoparticle carriers, as well as means to improve the targeting ability for concentration at the target site via vascular extravasation or by extravasation concurrent with cellular uptake, and lengthening the half-life of the resulting construct in the body. These and other objectives will be better understood with reference to the following disclosure.

SUMMARY OF THE INVENTION

The present invention is directed to magnetically responsive therapeutic carriers, their composition, preparation, and use. Magnetically responsive therapeutic carriers of this invention comprise single-domain magnetite nanoparticles having an average primary particle size ranging between 1 and 50 nanometers, and clusters of the single-domain magnetite nanoparticles, the clusters having an average cluster size ranging between 5 and 1000 nanometers. The nanoparticles are encapsulated with a silica coating to which is chemically bound a first silane coupling agent having a specific pendant functional group with a specific covalent binding capacity for the therapeutic. Inherent in the approach of this invention is the design of linker chemistries that allow for the controlled release of the therapeutic from the conjugate as a function of the ultimate localization of the construct. This aspect of the invention further separates the therapeutic carriers and methods of this invention from previous work conducted in the area, such as by Alexiou (Alexiou C, Arnold W, Klein R, Parak F, Hulin P, Bergemann C, Erhardt W, Wagenpfiel S, Lübbe A, "Locoregional Cancer Treatment with Magnetic Drug Targeting" *Cancer Res.*, 60, 6641-6648, 2000; Jurgons R, Seliger C, Hilpert A, Trahms L, Odenbach S, Alexiou C, "Drug Loaded Magnetic Nanoparticles for Cancer Therapy" *J. Phys.: Condens. Matter,* 18, 2006; and Johnson J, Kent T, Koda J, Peterson C, Rudge S, Tapolsky G "The MTC Technology: A Platform Technology for the Site-Specific Delivery of Pharmaceutical Agents" *European Cells and Materials*, Vol. 3. Suppl. 2, 2002 (pp. 12-15)).

In other embodiments, the therapeutic carriers additionally comprise the therapeutic bonded to the silane coupling agent, an aptamer to selectively bind with target cells, and a stealth agent for increasing the therapeutic carrier half-life. The stealth agent can optionally comprise a modification to the aptamer, the therapeutic, or the coupling agent.

A method of the present invention for making a magnetically responsive therapeutic construct comprises the following steps. Magnetically responsive iron oxide nanoparticles are formed and coated with a silicate material to form silica-coated magnetically responsive nanoparticles. A first silane coupling agent is bonded to the silica coating wherein the silane coupling agent has specific pendant functional groups with a binding affinity, preferably covalent, for the desired therapeutic, thereby forming nanoparticle therapeutic carriers. The nanoparticle therapeutic carriers are combined with a liquid containing the therapeutic to allow the specific pendant functional groups to chemically bond, preferably covalently, with the therapeutic and form a therapeutic construct. The therapeutic construct is separated from the liquid by applying a magnetic field.

The present invention also includes a method for delivering a therapeutic to a target cell within a body. The magnetically responsive carrier nanoparticles described above, chemically bonded to the therapeutic, and introduced into the body and moved to the target cell using a controllable magnetic field generator adapted to move the carrier nanoparticles in three dimensions. In other embodiments, the magnetic field generator produces a repetitively-varying magnetic field for moving the particles through tissue in the body.

Other features and advantages of the present invention will be readily apparent to those skilled in the art upon a reading of the description of preferred embodiments which follows.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1 is a diagrammatic illustration of the fixed-magnetic field experimental setup.

FIG. 2 is a diagrammatic illustration of a repetitively-varying magnetic field gradient experiment using a permanent magnet.

FIG. 6 shows images comparing i.v. and i.p. administration.

FIG. 7 shows magnetically responsive nanoparticles inside tissue.

DESCRIPTION OF THE PREFERRED EMBODIMENTS

Figure 3:
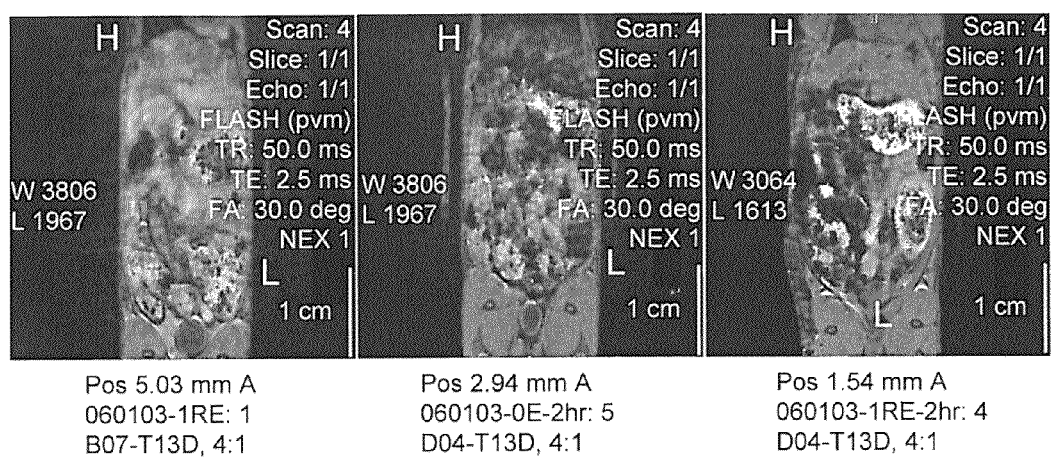
FIG. 3 shows representative coronal images of nude mice injected with magnetically responsive nanoparticles.

Targeted delivery of therapeutics to a specific site within a body provides advantages over oral or systemic administration. Drug delivery systems based on magnetically responsive nanoparticles provide a method for external control, and site-specific delivery of therapeutics. For example, the targeted therapeutic can be an existing or new drug or drug complex, whose physical-chemical properties, such as solubility and mobility, are not optimum in the physiological environment. Targeting through external magnetic forces overcomes this issue, and the therapeutic index of such drugs can be increased. A second advantage offered by this invention is the targeting of highly effective (and toxic) drugs to sites without collateral harm to healthy tissue, also resulting in an increased therapeutic index. The therapeutic index is defined as a comparison of the amount of therapeutic agent that causes the therapeutic effect to the amount that causes toxic effects. A high therapeutic index is preferable to a low one: this corresponds to a situation in which one would have to take a much higher amount of a drug to do harm than the amount taken to do good.

Due to the particle size, less than 500 nm and preferably, less than about 250 to 300 nm, the nanoparticle can be caused to extravasate through the tumor vasculature and possibly become internalized by the tumor or stromal cell, to enable therapeutic release intracellularly or within the tumor interstitial fluid. Importantly, the present invention offers a bimodal delivery means, whereby magnetic nanoparticles are used to concentrate a therapeutic construct at the target site, followed by enhanced cellular uptake due to the presence of focused or shaped magnetic forces, and/or the presence of biological moieties, such as aptamers or hyaluronic acid, that offer second stage affinity mechanisms for endocytosis of the therapeutic construct.

Magnetically Responsive Therapeutic Carriers

Magnetically responsive therapeutic carriers of this invention comprise magnetically responsive nanoparticles, a silica coating, and a silane coupling agent. The magnetically responsive nanoparticles include single-domain nanoparticles comprising magnetite, clusters of single-domain nanoparticles comprising magnetite, and mixtures of the two. The single-domain nanoparticles have an average particle size ranging between 1 and 50 nanometers and the clusters have an average cluster size ranging between 5 and 1000 nanometers. The single-domain nanoparticles are encapsulated by the silica coating. The silane coupling agent is bonded to the silica coating and has a specific pendant functional group capable of selectively binding with the desired therapeutic.

The magnetically responsive nanoparticles comprise magnetite and can be made using procedures known to those skilled in the art, and methods described in U.S. patent application Ser. No. 10/724,563 filed Nov. 26, 2003, now abandoned, and U.S. patent application Ser. No. 11/712,112 filed Feb. 28, 2007, both of which are incorporated herein by reference. Preferably, the single-domain nanoparticles, both individually and within clusters, comprise superparamagnetic magnetite. As understood by those skilled in the art, suspensions of ferromagnetic particles can become superparamagnetic when the particle size is reduced within the single domain range until a size is reached for which remanence and coercivity go to zero. The properties become similar to paramagnetic materials in that they show little or no remanence or hysteresis; however, their magnetic susceptibility is much higher and increases with cluster size and mass.

When clusters are present, preferably the magnetic moments of the single-domain nanoparticles are uniformly aligned within each cluster. Such clusters can be prepared by feeding an iron salt solution to a spray dryer equipped with a magnetic field generator. The feed solution is atomized into droplets in the drying chamber where the droplets are exposed to the magnetic field to encourage uniform alignment of the nanoparticle magnetic moments within each exposed droplet.

The magnetite nanoparticles and clusters of nanoparticles are coated with silica. The silica coating enhances biological stability and inertness, reduces particle-particle interaction, and allows access to silicon-based chemistry for particle conjugation to drug payloads as described in detail below. Suitable sources of silica include sodium silicate, potassium silicate, lithium silicate, aluminum silicate, zirconium silicate, calcium silicate, and silicic acid. Preferably, the silica source is sodium or potassium silicate. Although commonly referred to as "silica coating," it is understood by those skilled in the art that precipitated silica coatings may be partially hydrated.

The silane coupling agent is an organosilane compound having at least two different types of reactive groups bonded to the silicon atom in the molecule. One of the reactive group types on the silicon is an active functional group such as methoxy, ethoxy or acetoxy groups. As understood by those skilled in the art, silane coupling agents, preferably those containing three such active functional groups, bind well to the metal hydroxyl groups on most inorganic surfaces, especially if the surface contains silicon. With respect to this invention, it is believed that the alkoxy groups on the silane hydrolyze to silanols which coordinate with hydrated silica groups on the silica coating of the magnetite nanoparticle to form an oxane bond. These theories are believed to reflect the actual mechanisms; however, constructs and methods of this invention do not depend on the accuracy of these theories.

The other reactive group on the silane coupling agent used in this invention is a specific pendant functional group that is capable of selectively binding with therapeutic and reacts with the therapeutic to form a chemical bond, preferably covalent. Suitable pendant functional groups include, but are not limited to, epoxy, amino, phenyl, carboxyl, ester and mercapto groups. Preferably, the pendant functional group is a carboxyl or amino group, and more preferably, a carboxyl group for reasons discussed in detail below.

Suitable amino silane coupling agents include, but are not limited to, 3-aminopropyltrimethoxysilane available from Dow Corning Corporation. Amino silanes are readily treated with 5-fluorescein isothiocyanate to produce a fluorescently labeled construct. An alternate pathway for obtaining a fluorescent carrier is treatement of the silica-coated magnetite nanoparticles with N-(triethoxyoxysilylpropyl)dansylamide available from the Gelest Corporation (www.gelest.com).

Suitable silane coupling agents having pendant carboxyl groups include, but are not limited to, 10-(Carbomethoxy) decyldimethy methoxysilane, N-[3-trimethoxysilyl propyl] ethylenediamine triacetic acid, tripotassium salt as well as other silanes that can be formed with a carboxyl group or those that can be converted to a carboxyl group. Carboxyl terminated coupling agents can be added by, for example, reaction of the silica-coated magnetically responsive nanoparticles with an alkoxysilylpropyl ethylenediamine mono- di- or triacetic acid or the sodium or potassium salt thereof under nitrogen blanket conditions to produce carboxyl terminated silica coated nanoparticles. A preferred such coupling agent is N-(triethoxysilylpropyl)ethylenediamine triacetic acid trisodium salt commercially available from Gelest Corporation (www.gelest.com) 11 East Steel Road, Morrisville, Pa. 19067.

Another preferred silane coupling agent is alkoxysilylpropyl-O-polyethylene oxide urethane containing monomer units of polyethylene glycol (PEG) terminating in an alcohol function which has been oxidized to a carboxyl group. For example, silica-coated nanoparticles are reacted with N-(triethoxysilylpropyl)-O-polyethylene oxide urethane containing five monomer units of polyethylene glycol (PEG) terminating in an alcohol function. The alcohol function is then oxidized by potassium dichromate to yield carboxyl terminated groups. Such a coupling agent is commercially available in glycol form from Gelest Corporation. While specific silane coupling agents are named, it is understood that many modifications to their structure can be made without negating their use in this invention.

Therapeutics that can be delivered by the magnetically responsive carriers of this invention include, but are not limited to, chemotherapeutics, stem cells or genetic materials, such as DNA, RNA, and siRNA, plasmids, and oligonucleotides or proteins. In some cases, the therapeutic is modified to allow formation of a chemical bond between the therapeutic and the silane coupling agent. Many commercially available chemotherapeutics do not require modification and can bind "as is" to the silane coupling agent. Example chemotherapeutic agents which may be used either "as is", if appropriate functional groups are present, or with modification to include a functional group, include but are not limited to, aminoglutethimide, amsacrine, bleomycin, busulfan, capecitabine, carboplatin, carmustine, chlorambucil, cisplatin, cladribine, cyclophosphamide, cytarabine, dacarbazine, dactinomycin, daunorubicin, docetaxel, doxorubicin, epirubicin, etoposide, fludarabine, fludrocortisone, fluorouracil, hydroxycarbamide (or hydroxyurea), idarubicin, ifosfamide, interferon, irinotecan, leucovorin, lomustine, melphalan, mercaptopurine, mesna, methotrexate, mitomycin, mitotane, mitoxantrone, oxaliplatin, paclitaxel, pentostatin, procarbazine, raltitrexed, rituximab, streptozocin, temozolomide, teniposide, testosterone, thiotepa, topotecan, treosulfan, tretinoin, vinblastine, vincristine, vindesine, and vinorelbine.

In a preferred embodiment, the therapeutic comprises one or more pendant hydroxyl groups which can bind with a carboxyl group present on the silane coupling agent. Examples of chemotherapeutics having one or more pendant hydroxyl groups include taxanes, pentostatin, capecitabine, hydroxycarbamide, vinblastine and others. Suitable taxane therapeutics include, but are not limited to, paclitaxel, docetaxel, polyglutamic acid-paclitaxel, polyglutamic acid-docetaxel, and mixtures thereof. Preferably, the taxane comprises paclitaxel, polyglutamic acid-paclitaxel, polyglutamic acid-docetaxel, or mixtures thereof. An example of such a taxane is paclitaxel, available commercially from Sciphar Biotechnology No. 11, Tangxing Road, Xi'an, China.

In another preferred embodiment of the present invention, the therapeutic comprises one or more amine groups which bind with a carboxyl group present on the silane coupling agent. Examples of suitable chemotherapeutics comprising an amine group include, but are not limited to, carboplatin, oxaliplatin, aminoglutethimide, bleomycin, dactinomycin, hydroxycarbamide, methotrexate. Chemotherapeutics comprising both hydroxyl and amine groups are also quite suitable for use in this invention as either group may bind with a carboxyl group on the silane coupling agent.

Preferably, the magnetically responsive therapeutic carriers are additionally modified to bind to desired target cells. Such modification is achieved using an aptamer having a first site capable of selectively binding with the target cell. In general, aptamers are classified as either DNA or RNA aptamers (referred to also as nucleic acid aptamers and usually comprising short strands of oligonucleotides), or as peptide aptamers (generally a variable peptide loop attached at both ends to a protein scaffold). Nucleic acid aptamers are typically created by selecting them from a large random sequence pool. In 2001, the in vitro selection process was automated by both the Ellington lab at the University of Texas at Austin, and by SomaLogic, Inc. in Boulder, Colo. The aptamers produced bind to specific targets with a high specificity and affinity in a manner similar to monoclonal antibodies. However, unlike monoclonal antibodies, the nucleic acid aptamers are synthetically derived which makes their production more predictable, reproducible and cost-effective.

Peptide aptamers are selected from an initial pool of around 10 million for their ability to bind the desired target, often using the yeast two-hybrid system known to those skilled in the art. The variable peptide loop of the aptamer typically comprises 10 to 20 amino acids. The bacterial protein Thioredoxin-A is often used as the scaffold protein, and the variable peptide loop is inserted within the reducing active site. Each selection identifies a panel of aptamers that "interrogate" the surface of the target protein. The selected peptide aptamer molecules typically retain their binding capacity when expressed in cellular or animal models and are not toxic.

Development of aptamer-based therapeutics has been rapid. In 2004, the FDA approved an aptamer-based drug for treatment for age-related macular degeneration (AMD), called Macugen offered by OSI Pharmaceuticals. The pegylated aptamer specifically targets and binds to vascular endothelial growth factor (VEGF 165), a protein that plays a role in angiogenesis and the abnormal blood vessel growth and leakage that characterize wet age-related macular degeneration AMD. In addition, Archemix in Cambridge, Mass., is developing aptamer-directed therapeutics with ARC1779 being evaluated in patients diagnosed with Acute Coronary Syndrome and undergoing Percutaneous Coronary Intervention.

The aptamer used in this invention preferably has a second site capable of linking it to the carrier. More preferably, the aptamer either has, or is modified to have, this second aptamer site capable of selectively binding with the specific functional group on the first silane coupling agent. For example, a hydroxyl or amine site on the aptamer will bind to a pendant carboxyl group on the first silane coupling agent. $NH_2$-modified aptamers are well known to those skilled in the art.

In an alternate arrangement, a second silane coupling agent is chemically bonded to the silica coating on the magnetically responsive nanoparticle surface. The second silane coupling agent preferably has pendant functional groups different from that of the first silane coupling agent and can thus bind specifically to the aptamer, while the first silane coupling agent binds specifically to the therapeutic. For example, a therapeutic having an amino group such as bleomycin is bound to a first silane coupling agent with pendant carboxyl groups, while aptamer oligonucleotides are covalently attached to pendant hydroxyl groups on a second silane coupling agent.

In yet another arrangement, the aptamer is covalently bound to pendant, preferably, hydroxyl, groups present on the therapeutic. For example, a silane coupling agent having pendant carboxyl groups, such as N-(triethoxysilylpropyl)ethylenediamine triacetic acid trisodium salt, is bonded to the silica coating on the nanoparticle surface to attach a therapeutic such as paclitaxel which has multiple hydroxyl groups per molecule. After one or more hydroxyl groups on the paclitaxel therapeutic are bonded to the pendant carboxyl groups on the silane coupling agent, aptamer oligonucleotides are then covalently attached to unlinked hydroxyl groups on the paclitaxel therapeutic.

It is known that non-modified aptamers are rapidly cleared from the bloodstream, often having a half-life of minutes to hours. In the case of nucleic acid aptamers, this can be due to nuclease degradation and clearance from the body by the kidneys. In some applications, such as treating blood clotting or treating organs where local delivery is possible, this rapid clearance can be tolerated. However, an increased half-life is necessary for most applications and several modifications, such as 2'-fluorine-substituted pyrimidines, polyethylene glycol (PEG) linkage, and others known to those skilled in the art, are available and known to increase the half-life of aptamers easily to the day or even week time scale.

Aptamers modified in the manner described above should increase the half-life of the entire therapeutic carrier. However, magnetically responsive therapeutic carriers comprising PEG units, such as the N-(triethoxysilylpropyl)-O-polyethylene oxide urethane containing five monomer units of polyethylene glycol (PEG) terminating in an alcohol function oxidized to carboxyl groups discussed above, are also known to block protein interactions and therefore, provide necessary half-life extension. As understood by those skilled in the art, PEGylation confers significantly improved half-life and reduced immunogenicity effects to macromolecules in the body, and most significantly for the present invention, to macromolecules in the body of primates.

A preferred magnetically responsive therapeutic carrier of this invention comprises magnetically responsive nanoparticles (individually, clustered, or both) having a silica coating. The construct has a silylpropylethylenediamine triacetate linker that has been reacted with a paclitaxel moiety to form a complete construct. Carbon analysis confirms the attachment of the paclitaxel to the linked silica coated magnetic nanoparticle.

Methods of Preparation

Methods of this invention for making a magnetically responsive therapeutic constructs basically comprise forming magnetically responsive iron oxide nanoparticles, coating the nanoparticles with a silicate material, and bonding a silane coupling agent in solution to the silica coating. The therapeutic construct is chemically bonded to the coupling agent and the resulting therapeutic carrier is separated from solution using a magnetic field.

The magnetically responsive magnetite nanoparticles and can be made using procedures known to those skilled in the art. Preferably, conditions are optimized such that the iron oxide nanoparticles produced comprise single-domain magnetite particles, and more preferably, superparamagnetic, single-domain nanoparticles. Preferably, the magnetite nanoparticles are prepared using a solution of ferric chloride and ferrous chlorides in a molar ratio of between 2 to 1 and 10 to 1, and an aqueous alkaline solution comprising ammonium hydroxide. The combination of the iron salt solution and the alkaline solution results in a gelatinous precipitate that may be isolated from the solution by centrifugation or magnetic decantation without washing with water. The gelatinous precipitate may be peptized with, for example, tetramethyl-ammonium hydroxide to form a stable alkaline magnetic solution or nanodispersion. The precipitate can then be washed with a solvent-like acetone and collected with a magnetic field.

Although these nanoparticles demonstrate a primary particle size of 10 to 20 nm utilizing TEM and XRay analysis, aqueous redispersions can produce agglomerates with size ranges exceeding 300 nm, making them generally unsuitable as vehicles for extravasation and endocytosis. In one embodiment, the magnetically responsive magnetite nanoparticles are subjected to high shear for deagglomeration prior to silica surface treatment. An example of high shear treatment includes, but is not limited to, high shear bead milling. Suitable agitated media mills are known to those skilled in the art. For example, one such suitable mill is a bead mill manufactured by and available from Netzsch, Inc. The North American subsidiary of the Netzsch operating companies is located in Exton, Pa.

The magnetically responsive magnetite nanoparticles and clusters, with or without high shear treatment, are silica coated by preparing a feed stock comprising a silica source and the magnetically responsive nanoparticles and clusters. The feed stock is mixed using standard procedures known to those skilled in the art to cause a layer of silica to precipitate on the surface of the nanoparticles.

In another embodiment, preparation of nanoparticle clusters and the silica coating application are performed using processes described in co-pending U.S. patent application Ser. No. 11/712,112, incorporated herein by reference. A feed stock is prepared comprising a silica source and the magnetically responsive nanoparticles suspended in a solvent. The feed stock is directed to a spray dryer equipped with a drying chamber, an atomizer for atomizing the feed stock into droplets, a source of heated drying gas for drying the droplets, and a magnetic field generator for exposing the droplets to a first magnetic field while in the drying chamber. The feed stock is atomized into droplets in the drying chamber where the droplets are exposed to the magnetic field to encourage uniform alignment of the nanoparticle magnetic moments within each exposed droplet and therefore, more uniform alignment of the nanoparticle magnetic moments in the resulting nanoparticle cluster. Drying of the droplets by the heated drying gas forms magnetically responsive nanoparticle clusters coated with silica.

Suitable sources of silica include sodium silicate, lithium silicate, aluminum silicate, zirconium silicate, calcium silicate, and silicic acid. Preferably, the silica source is sodium silicate. Encapsulation of the nanoparticle with silica provides a biocompatible surface that inhibits free radical generation from iron oxides (Fenton chemistry) and provides a substrate for attachment of silane linker containing reactive functional groups, which are further covalently modified with aptamers, to promote endocytosis, and the therapeutic, which is cleaved in the cell, following extravasation and endocytosis.

The procedure for coating the nanoparticles with silanes depends on the specific silane used, but are generally known to those skilled in the art. Examples 3 and 4 below, outline methods for attaching 3-aminopropyl trimethoxy silane and other silanes such as N-trimethoxysilylpropyl-N,N,N-trimethylammonium chloride, and 10-(carbomethoxy)decyldimethylmethoxysilane to the silica coated magnetically responsive nanoparticles.

In a preferred mode, the silica coated nanoparticles are reacted with a solution containing N-(triethoxysilylpropyl) ethylenediamine triacetic acid trisodium salt, ethanol and acetic acid. The hydrolyzable ethoxy groups on the silane coupling agent bond to the silica coating leaving the carboxyl groups extending from the particle surface. In another preferred mode, the silica coated nanoparticles are reacted with a solution containing N-(triethoxysilylpropyl)-O-polyethylene oxide urethane, ethanol and acetic acid. The hydrolyzable ethoxy groups again bond to the silica coating with the polyethylene glycol (PEG) groups extending from the surface and terminating in a hydroxyl group. The product is oxidized with, for example, potassium permanganate to convert the hydroxyl terminating group to a carboxyl, thus producing carboxyl terminated oxidized (PEG) silanes.

The carboxyl function on the attached silane is activated for the attachment of a therapeutic hydroxyl or amine group by reaction with a carbodiimide. The particular carbodiimide depends on the ultimate solubility of the specific carboxyl silane used as the precursor adduct. An aqueous reaction using 1-ethyl-3-(3-dimethylaminopropyl)-carbodiimide in a Hepes buffer solution is preferred for the activation of an attached hydrophilic silane such as 10-(Carbomethoxy)decyldimethy methoxysilane. Reaction with N,N'-Dicyclohexylcarbodiimide in methylene chloride is preferred for activation of attached carboxyl terminated oxidized (PEG) silanes.

Methods for Delivering a Therapeutic to a Target Cell

In medical treatment applications of this invention, magnetically responsive nanoparticle therapeutic carriers and constructs, as described in detail above, are first introduced into the body, and then caused to move to the target cell(s) using a controllable magnetic field generator adapted to move the carrier nanoparticles in three dimensions. Using magnetically vectorable chemotherapeutic constructs, for example, can provide higher drug levels at the tumor, which can result in enhanced cancer cure and survival rates.

The magnetically responsive nanoparticle therapeutic constructs may be introduced into the body by injection or infusion, including intraarterial, intravenous, intraperitoneal, or intratumoral routes. In a preferred mode, the constructs are introduced systemically, for example, via an intra-tumor arterial route (I.a.). More preferably, the constructs are administered to the body by injecting into the bloodstream intravenously (i.v.).

The single domain and superparamagnetic nanoparticles of this invention respond to an applied magnetic field, but rapidly return to an unmagnetized state without remanence or hysteresis when the field is removed. Three-dimensional vectoring of the nanoparticles and constructs occurs by controlling the shape of the magnetic field, through manipulation of the x, y, z directional components of the field, to focus the gradient on target cells or tissues. Electromagnetic instrumentation for the vectored navigation of the constructs and concentration of the constructs at the target area is available commercially from, for example, Electromagnetic Interventional Workstation, Stereotaxis Corp, St. Louis, Mo., which is presently used for catheter placement in cardiac ablation surgery. The unit directionally navigates the catheter across short distances in a uniform magnetic field.

Once the particles have been concentrated at the target area, the particles must penetrate the target organ or tumor and often must penetrate or be delivered through additional tissue adjacent the target cells. For example, nanoparticles carrying cancer treating drugs can be carried in a carrier fluid such as the blood stream to a target tumor. In this case, the nanoparticles must be moved from the bloodstream through membranes such as the wall of a blood vessel including the endothelium, as well as the membrane or tissue containing and surrounding the tumor cells. The term "membrane" is used herein and in the appended claims in a broad sense to include arterial and vein walls as well as any tissue covering, lining, containing or separating target organs, tumors, cells, and the like in the body. The rate and extent of membrane penetration are critical parameters for optimum performance of these applications.

Conventional procedures to pull magnetically responsive particles through a fluid or tissue use fixed or permanent magnets to pull continuously in the same direction. Using a fixed magnet, the particles can be moved through a membrane, but the movement is relatively slow. A discovery outlined by U.S. patent application Ser. No. 11/400,620 filed Apr. 6, 2006, is that the rate of movement of superparamagnetic nanoparticles through a membrane is significantly faster using a magnetic field that oscillates or varies repetitively in direction and/or in strength, and particularly when using a field in which the direction of the magnetic field gradient varies repetitively with time. Thus, an embodiment of the present invention comprises introducing magnetically responsive nanoparticles into the body, and influencing nanoparticle movement and concentration at a site using a repetitively-varying magnetic field directed at the target site.

The phrase "repetitively-varying magnetic field", as used herein and in the appended claims, is defined as "a magnetic field having repetitive changes or perturbations in the direction or strength of the magnetic field gradient or both." Varying the direction of the magnetic field gradient causes the force acting upon magnetic particles to vary in direction so as to aid particles in moving around individual molecules or fibers making up a vascular membrane and tissue. The particles can also be periodically relaxed by the magnetic field so as to disengage from the structure of the tissue and be free to move in the gradient when it is reestablished. These theories are believed to reflect actual mechanisms; however, the devices and methods of the invention do not depend on the accuracy of these theories.

Suitable magnets include both permanent magnets and electromagnets. Commercially available permanent magnets include magnetic metallic elements, composites such as ceramics and ferrites, and rare earth magnets. Electromagnets are also readily available commercially.

In one embodiment, the device comprises at least one electromagnet such that the magnetic strength can be oscillated or pulsed. (The term "oscillate" and all its forms are used broadly to include a pulse.) For example, the magnetic field can be oscillated by controlling an electrical switch to oscillate power to the electromagnet. Design of electromagnets suitable for applications requiring oscillation and pulsing is well known to those skilled in the art.

An example magnetic field generator and arrangement includes, for example, two pulsed electromagnets separated by a permanent magnet supplying at least about 50% of the magnetic field directed toward the target cells. Another design includes two electromagnets directed parallel to, or at an angle to, the permanent magnet and a controller that is adapted to alternately pulse the electromagnets. Yet another design comprises three or more oscillating electromagnets surrounding and parallel to a permanent magnet supplying at least about 50% of the magnetic field.

The positioning means is preferably a controlled mechanical arm adjustably attaching the magnet(s) and providing stability and controlled positioning with respect to the membrane. Such positioning means are well known to those skilled in the art and are used, for example, in angioplasty procedures for remote guidance of intravascular catheters. As described above, suitable electromagnetic instrumentation is available commercially from, for example, Stereotaxis Corp. located in St. Louis, Mo.

Cancer Treatment

In another embodiment, this invention includes a method of treating cancer in a subject. The therapeutic constructs described above are administered to the subject having cancer. Nonlimiting examples of suitable therapeutics include a taxane such as paclitaxel, docetaxel and mixtures of the same Paclitaxel is an anti-microtubule agent extracted from the Pacific yew tree and is effective against advanced ovarian and breast cancer. Its usefulness has also been reported for small-cell and non-small cell lung cancer, head and neck cancers, and malignant melanoma. Docetaxel is semisynthetically produced and has been shown to be effective in treating cancers including breast, lung, ovarian, head and neck, colorectal cancers and melanomas. However, both paclitaxel and docetaxel use have been limited by their poor water solubility as well as by their toxicity.

Recently, compositions comprising conjugates of paclitaxel and poly-glutamic acid, and docetaxel and poly-glutamic acid, have been shown to have excellent antitumor activity in animal models, while exhibiting much improved pharmaceutical properties. Loading these drugs onto magnetically-vectored nanoparticles, as described in previous sections, allows the drugs to be tumor-targeted to provide even greater patient benefit. Preferably, the specific pendant functional group on the silane coupling agent is a carboxyl group and the therapeutic, comprising paclitaxel, docetaxel, mixtures and poly-glutamic acid conjugates thereof, is bonded to the silane coupling agent through ester linkages. The controllable magnetic field generator may be used to hold the therapeutic constructs proximate to the target cells until either extravasation or endocytosis occurs.

The magnetically-vectored therapeutic constructs of this invention are understood to be effective against any type of cancer for which the therapeutic alone is shown to be effective. For paclitaxel and docetaxel these cancers include, but are not limited to, breast cancer, ovarian cancer, malignant melanoma, lung cancer, head and neck cancer. The therapeutic constructs of this invention may also be used against gastric cancer, prostate cancer, colon cancer, leukemia, or Kaposi's Sarcoma. As used herein and in the appended claims, the term "treating cancer" is defined as any medical management of a subject having a tumor, and thus includes any attempt to inhibit, slow or abrogate tumor growth or metastasis, as well as killing a cancer cell by apoptotic or non-apoptotic mechanisms of cell death.

In order to further illustrate the constructs, methods and systems of the present invention, the following examples are given.

EXAMPLE 1

An aqueous solution of ferric chloride ($FeCl_3$) was mixed with an acidic solution of ferrous chloride ($FeCl_2$) in a molar ratio of 2:1. The water used to make all solutions was degassed by bubbling nitrogen throughout the water for a minimum of 45 minutes prior to making any solutions used in the synthesis. The resulting iron solution was gently stirred under a nitrogen blanket for approximately 15 to 30 minutes. The iron chloride mixture was then added, at a controlled rate, to an aqueous ammonia solution to form a precipitate. The mixture was then stirred for 30 minutes with continued bubbling of nitrogen through the solution, and the precipitate was collected using a magnetic field. The precipitate was washed several times in distilled water to remove salt products produced by the reaction.

The above process produced superparamagnetic nanoparticles comprising magnetite having a magnetic susceptibility of greater than 35-40 emu/g. The nanoparticles were characterized using X-ray diffraction (XRD), which analysis revealed the presence of magnetite particles having an average diameter of 10 nanometers. The diameter of the magnetite particles was confirmed using Transmission Electron Microscopy (TEM). Observation of the uncoated magnetite particles using High Resolution Transmission Electron Microscopy further established the existence of magnetite particles.

Encapsulation of the nanoparticles with silica was achieved using the following procedure. The above-prepared suspension of magnetite nanoparticles was stirred and a 4 mL aliquot was taken up to 100 ml with distilled water. A solution of 0.54% sodium silicate was prepared at a pH of 10.5, and 4 mL of the sodium silicate was added to the magnetite nanoparticle suspension. The pH of the resulting suspension was adjusted to 10.0 with HCl and stirred for 2 hours. The reaction system was allowed to stand for 4 days, collected by a magnet and washed with distilled water several times. It should be noted that equivalent product is obtained by adjusting the pH to 9.0 rather than 10.0, stirring for 2 hours, and then dropping the pH to 7.0 with HCl and stirring for 2 hours. The silica-coated magnetite nanoparticles produced in this manner had a magnetic susceptibility greater than 20 emu/g while having an average diameter of less than 50 nanometers.

EXAMPLE 2

A method referred to as "Ultrasonic Liquid Atomization" (ULA) was used to produce clusters of nanoparticles and silica-coated nanoparticles having a controlled cluster size and size distribution. In bench scale tests, a sonicated (~50 W) dispersion of nanoparticles, in aqueous or other media, were spray dried in Buchi mini spray dryer using an ultrasonic nozzle (>200 KHz). A silica cementing agent or other surface treatment compounds, such as organic polymers, were added to the nanodispersion in the correct stoichiometry to produce the desired coating thickness and passed through the ultrasonic nozzle. The ultrasonic nozzle produces and injects an aerosol spray of uniform droplet size and size distribution into a 6-inch diameter drying chamber. In the drying chamber, heated air is flowed co-currently at a flowrate sufficient to remove the dispersion solvent and carry the dried nanoparticles to a cyclone separator and collection chamber. In several tests, the drying chamber was fitted with a magnetic collar at the point of entry of the aerosol spray to aid in uniform alignment of the magnetic moments of the nanoparticles prior to cluster formation in order to maximize the magnetic susceptibility of each formed nanocluster. The magnetic collar consisted of a leather belt with four ceramic magnets radially and uniformly arranged to point toward the central axis of the drying chamber. As shown in Table I below, the magnets did improve the magnetic susceptibility of the nanoparticle clusters.

The cyclone collection chamber was also fitted with a magnet which visibly and significantly aided in collection and retention of the nanoparticle clusters.

TABLE I

Results of Spray Dryer Magnetic Field on Cluster Magnetic Susceptibility

| Test Number | Magnetic Field yes/no | Magnetic Susceptibility emu/g |
|---|---|---|
| 1-92 #1 | No | 35 |
| 1-92 #2 | Yes | 23 |
| 1-95 #1 | No | 9 |
| 1-96 #1 | Yes | 14 |

EXAMPLE 3

The biocompatibility and hermeticity of silica-coated magnetite nanoparticles, as a function of particle free radical generation, were assessed by three methods that included Electron Sip Resonance which is based on the Fenton system known to generate free radicals and these radicals are trapped by DMPO (5,5-dimethyl-1-pyrroline-N-oxide). Results indicated no evidence for free radical generation.

The effect of silica-coated magnetite nanoparticles on cell toxicity and viability (in vivo compatability) was assessed with guinea pigs implanted with nanoparticles in epithelial tissue of middle ear organs. After 8-15 days of implantation, a board-certified veterinary pathologist noted no difference in tissue inflammation and/or particle degradation compared to the control group. These results provide evidence that the silica-coated magnetically responsive nanoparticles of this invention can resist biological degradation.

EXAMPLE 4

It was speculated that magnetic particles show a slow response to a continuous magnetic field when pulled through a membrane due to simple misalignment with pores in the membrane. Particles could also become trapped on the wall of channels going through the membranes, or in fibrous membranes, the particles could become entangled in the fibers as they move through. Changing direction of particle movement could assist particles to realign, to move past matter that accumulates in front of the particles, or to move off the wall of the pores as the particles are being pulled through the membrane.

Also, the probability of the particles becoming attached to the wall of a pore is greater when the maximum magnetic gradient is at a significant angle to the axis of the pore. Therefore, changing the angle of the magnetic gradient should result in moving the particles off the wall of the pore. Similarly, shutting off the magnetic field should allow the particles to diffuse off the wall of the pore and thus become free to move through the tissue.

Laboratory tests using a fixed, constant strength magnet were performed to determine the base case feasibility of moving magnetic particles through membranes. A test apparatus 10 was arranged as shown in FIG. 1. The objective of the test was to pull magnetic (magnetite) nanoparticles 12 present in the first chamber 14 through a porous membrane 16 and into a second chamber 18. A stationary electromagnet 20 was used to pull the magnetite nanoparticles 12 from a carrier fluid 22 in first chamber 14, across porous membrane 16, and into a clean fluid 24 in second chamber 18. Power to the electromagnet 20 remained constant and the test ran for several hours. The results, evaluated visually, established that very few particles penetrated the porous membrane 16. It was concluded that the particles moved relatively slowly through the membrane.

A second test was then performed using a magnetic field that varied in strength. This test also utilized a test apparatus 10 as shown in FIG. 1, except that the electromagnet 20 was operated in a pulsing or on/off mode. This was achieved by connecting the electromagnet 20 to a controller having a switch and timer to turn the electromagnet 20 on and off. The pulsation presumably allowed the particles to be released from membrane fibers or the walls of pores by diffusion.

A third laboratory test was run in which the direction of the magnetic gradient was varied. The test assembly 25 is shown in FIG. 2. In this modification, a permanent magnet 26 was attached to a steel rod 28 having two right angle bends 30. One end of the rod 28 was then attached to an electric motor 32 so that the magnet 26 could be rotated at an estimated 30 to 60 rpm. Rotation of the magnet 26 causes the components of the magnetic gradient parallel to the face of the magnet 26 to vary.

The second and third tests were also performed for several hours. The results were that significant quantities of particles appeared on the second chamber side of the membrane in both the second and third test. Also, significant quantities of particles were pulled to the bottom of the second laboratory chamber 18 in the third test. It was concluded that pulsation of the magnetic field and oscillating the magnetic field component perpendicular to the direction the particles are to be moved enhances particle movement through the laboratory porous membrane. Since varying the direction or strength of a magnetic field gradient aids the movement of particles through a laboratory porous membrane, it is likely the same effect will be operative in moving particles through living tissue or membrane.

EXAMPLE 5

The procedure for coating of nanoparticles with silanes depends on the specific silane used. For 3-aminopropyl trimethoxy silane, the following procedure, as outlined by Wong et al, Journal of Young Investigators (6), 2002, was used. A 1 mL suspension of the silica-coated magnetite prepared, as in Example 2 above, was removed and the aqueous layer of the suspension was separated by aid of a magnet. Distilled water was then added (5 mL) to the silica-coated magnetite. A 5% solution of 3-aminopropyl trimethoxy silane was prepared by adding the silane directly to the silica-coated magnetite and then diluting to a 10 mL final volume with water. The system was stirred and allowed to react at room temperature for 1 hour with occasional stirring, after which the coated nanoparticles were washed with distilled water using a magnet to aid separation of nanoparticles from the wash water. A Kaiser assay was performed on several of the functionalized nanoparticles to confirm the presence of amine groups on the surface of the silica-coated nanoparticles.

EXAMPLE 6

For other silanes such as N-trimethoxysilylpropyl-N,N,N-trimethylammonium chloride, 10-(carbomethoxy)decyldimethylmethoxysilane, etc., the following procedure was used for coating nanoparticles. A 200 mL quantity of 95% ethanol solution was prepared and, if the silane used did not contain an amine group, the pH was adjusted to between 4.5 and 5.5 with glacial acetic acid. If the silane did contain an amine group, then the pH adjustment was omitted. A 1% to 2% solution of the silane was prepared in the 95% ethanol solution and allowed to hydrolyze for a minimum of five minutes. A 500 mg sample of silica-coated magnetite prepared, as in Example 1, was added to the silane solution and allowed to react for 2 hours with stirring. The material was then washed with ethanol using a magnet to aid separation of the nanoparticles. Carbon analysis indicates the attachment of the organosilane to the silica-coated nanoparticle.

EXAMPLE 7

Attachment of paclitaxel to a carboxyl terminated magnetic nanoparticle can be achieved utilizing the carboxyl groups of the nanoparticle as the point of attachment in a reaction with the hydroxyl groups of paclitaxel. A 0.35 g sample of a carboxyl terminated silica coated magnetite nanoparticles is suspended in water. The pH is adjusted to 2.0 with HCl and then this is placed into a dialysis bag and dialyzed against water. After dialysis, the material is collected and then 0.075 g of the carboxy terminated material is suspended into 1.5 mL of dry N,N-dimethylformamide. To this suspension, 27.7 mg of paclitaxel is added and the suspension is then shaken. Dicyclohexylcarbodiimide (20.7 mg) is added and again the reaction system is shaken. A trace amount of dimethylaminopyridine is added as a catalyst and the reaction system is allowed to react for 22 hours at room temperature with shaking. Several mL of chloroform are added to stop the reaction and the chloroform is allowed to remain on the nanoparticles for approximately 45 minutes. The particles are then washed with acetone using a magnet to aid in separation. Carbon analysis of the purified finished product confirms the attachment of paclitaxel to the nanoparticle.

EXAMPLE 8

Experiments with silica-coated magnetic nanoparticles prepared as above (MNPs) were conducted in normal (non-tumor-bearing) female nude mice, the hosts for subsequent experiments with implanted human ovarian carcinoma xenografts. These experiments were intended to determine whether these MNPs demonstrated sufficient magnetic susceptibility to move under the influence of the fields from readily available permanent magnets. Because these particles also function as ultra-small paramagnetic iron oxides, a class of contrast agents that are known to cause easily recognizable artifacts in magnetic resonance imaging (MRI) measurements, MRI was used to non-invasively visualize the distribution and movement of particles over time. All MRI measurements were made using a 4.7T Biospec small animal MRI system (Bruker Biospin MRI, Billerica, Mass.) with standard gradient (60 mm I.D.) and volume RF coil (35 mm I.D.) configurations. Animal anatomy and particle distribution was visualized using multi-slice T1—(TE/TR 8.5/620 ms), T2—(TE/TR 60/300 ms), and multi-echo T2*-weighted (TE/TR 3.5,12.2,20.9/500 ms, 45° flip angle) sequences along with a 3-dimensional T1-weighted (TE/TR 2.5/50 ms, 30° flip angle) acquisition. For multi-slice acquisitions, a field-of-view (FOV) of 50×37.5 mm was acquired over a matrix of 256×192 points with a slice thickness of 1 mm and a 0.25 mm gap between slices. The FOV of the 3-dimensional scans was 50×37.5×24 mm over a matrix of 256×192×24 points.

Following in vitro magnetic resonance imaging (MRI) phantom experiments to determine what concentrations of particles were likely to be effective in causing image artifacts in vivo, 150 μL of 1000 μg/ml concentrations of these MNPs were injected i.p., followed immediately by placement of a 22 mm diameter cylindrical Nd/B/Fe magnet (Arbor Scientific), rated at 5600 Gauss at its face surface, to the right of the mouse abdomen for 2 hours. During this time, the mouse was resting on its anterior, under monitored isoflurane inhalation anesthesia. Control mice did not have a magnet in place, but otherwise were treated the same and for the same duration. Coronal and sagittal, T1-, T2-, and T2*-weighted MRI images were obtained pre-injection and immediately following the magnetic localization.

Representative T1-weighted, 3-dimensional coronal images are shown in FIG. 3. The image on the left is taken pre-injection, showing normal peritoneal anatomical features in this slice. The image in the middle is taken after a mouse was injected with MNPs and left under anesthesia with no magnet in place for 2 hours; it shows wide dispersion of the MNPs left in the peritoneum. The image on the right is from a mouse similarly injected, but with the magnet placed to the right (left on image) of its abdomen. MRI evidence for accumulation of MNPs near the juxtaposed magnet is clear. Thus, it is clear that the magnetic susceptibility of these MNPs and the field strength of this magnet were sufficient to cause MNP movement within the dimensions relevant to the peritoneum of a normal mouse.

EXAMPLE 9

Further studies were performed using a tumor-bearing mouse. The tumor model focused on initially was the HEY human ovarian carcinoma. In contrast to the poly-focal presentation of carcinomatosis, characteristic of initial presentation of Stage III disease, the HEY i.p. xenograft grows focally, with frank disease within the peritoneum, and also with a major, primarily solitary lesion in the injection needle-track in the anterior abdominal wall, that progresses to invade the peritoneum. This is more akin to the focal disease that can occur with relapsing disease.

In the first experiment in this model, we i.p.-injected an identical load of MNPs to that used in the preceding normal mouse study. These MNPs were also labeled with FITC to allow post-mortem particle localization by fluorescence microscopy to be conducted on tissue sections. In this setting, the same cylindrical magnet was suspended above the mouse abdomen with the anesthetized mouse lying on its back for 2 hours immediately post-MNP injection. The cylinder axis was aligned with and the magnet face placed proximally to the i.p. tumor needle-track from tumor cell inoculation 2-3 weeks earlier, as this growth was evident subcutaneously on the abdomen. The control, tumor-bearing mouse did not use this magnet for the same duration. Due to the position of the tumor in the abdomen, sagittal rather than coronal T1- and T2-weighted MRI images were obtained, which offered a better view.

Figure 4:
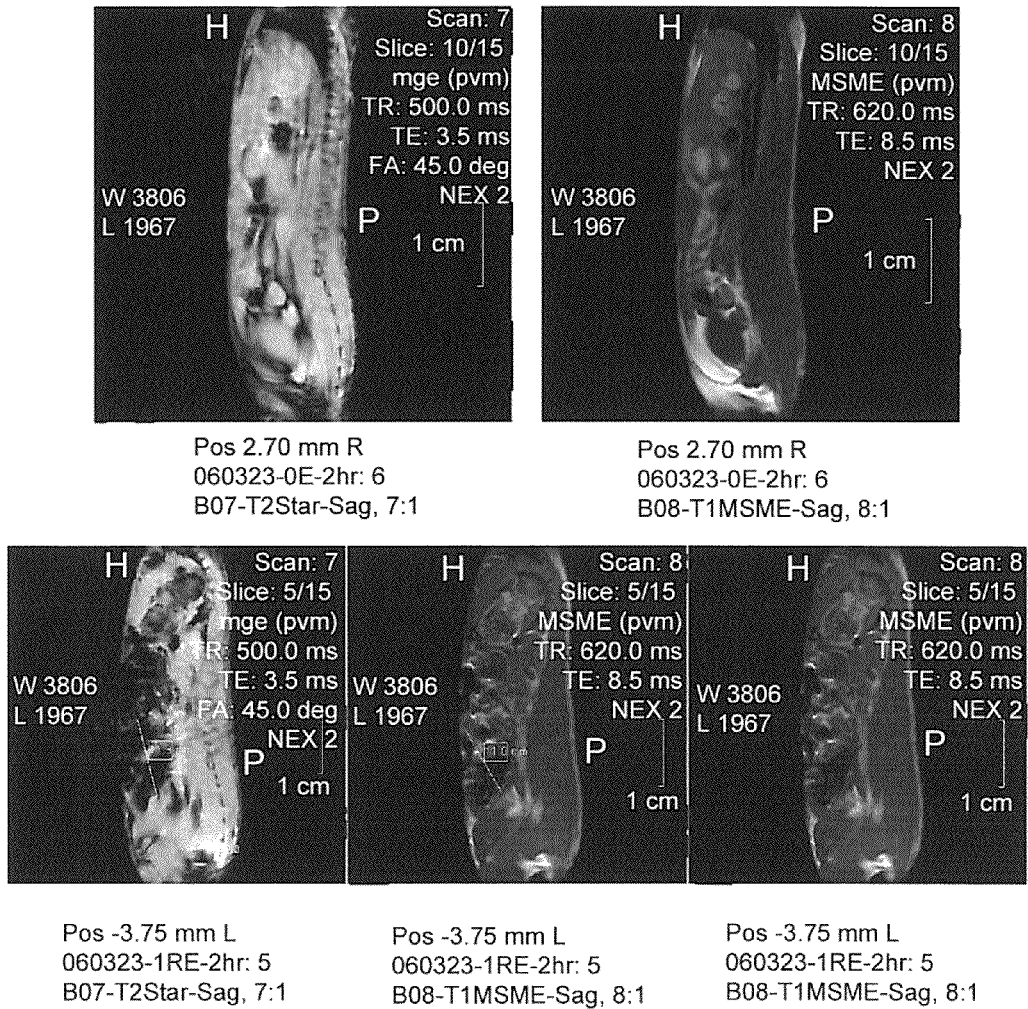
FIG. 4 is a set of images showing results of magnetic vectoring in tumor-bearing mice.

The resulting T1- and T2*-weighted images are shown in FIG. 4. The two images on top were taken 2 hours post-injection, without a magnet in place over the anesthetized mouse. The T1-weighted image on the top right shows the prominent outline of the tumor in the anterior abdominal wall, and the T2*-weighted image on the top left shows little discernable evidence for MNP accumulation in any tissue in this slice. The three images on the bottom were taken 2 hours post-injection, with the magnet in place over the tumor of the anesthetized mouse for the full duration. The T2*-weighted image on the bottom left shows marked signal ablation due to MNP accumulation in the tumor/peri-tumoral area and neighboring abdominal wall. The scalar is inserted for orientation of the distance between bladder and tumor centers on this image and the image in the middle. The two T1-weighted images on the bottom middle and right display clear susceptibility artifacts characteristic of signal distortion due to ultra-small paramagnetic iron oxides; the middle image again shows the scalar for orientation, as well as a marker for the tumor center, while the image on the right is native. Thus, based on these MRI imaging results, it seems clear that these MNPs can be vectored to the tumor/peri-tumoral area in this model.

EXAMPLE 10

Figure 5:
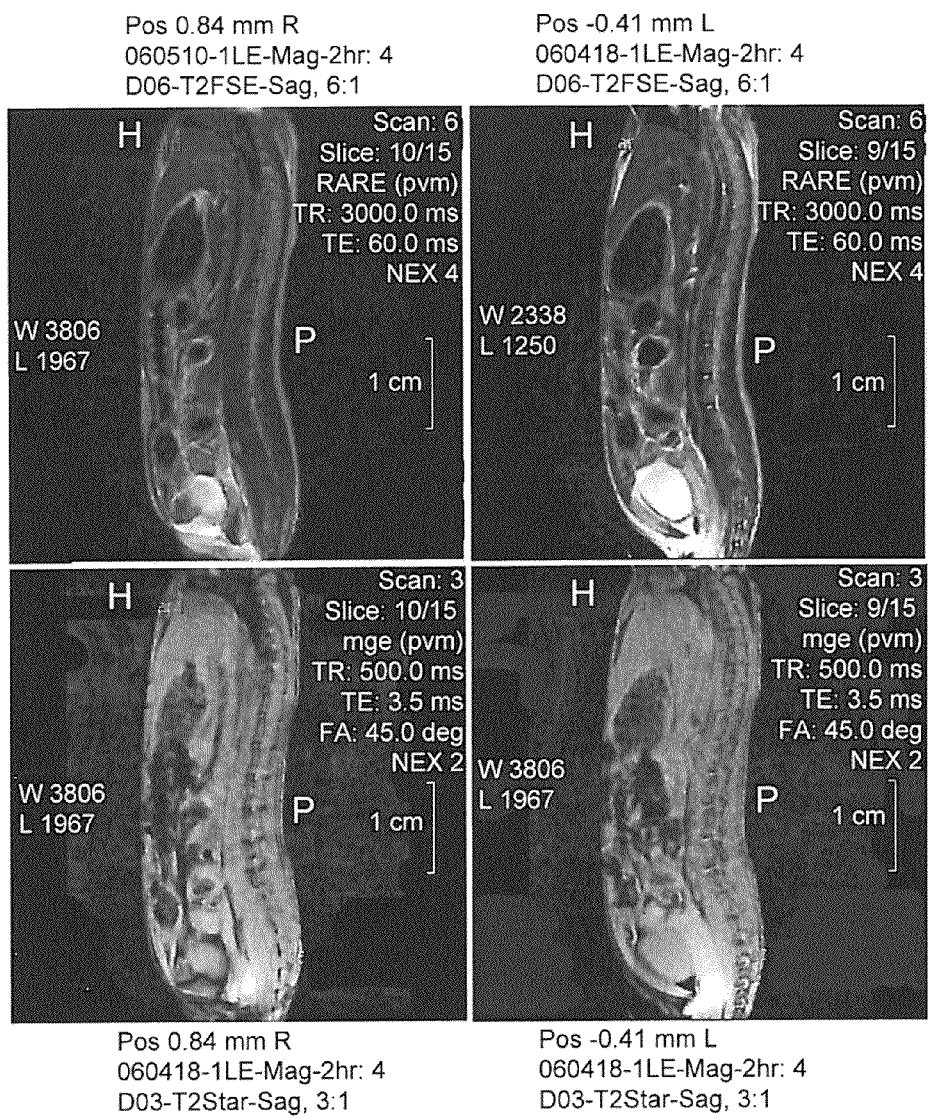
FIG. 5 shows results of magnetic vectoring in mice using a different magnet configuration.

Although there was convincing MRI evidence for significant movement of the MNPs to the tumor/peri-tumoral area, there was also substantial accumulation apparent near normal tissues such as the abdominal wall, likely due to the wide bore of the magnetic field of the 22 mm magnet. Since this would likely be a source of future toxicity if these MNPs were drug-loaded, tests were run to determine whether use of a similarly-powered, but more focused magnetic field, might improve MNP localization. For this purpose, we used a pyramid-shaped magnet (K and J Magnetics) that has a flat peak surface of ~3×3 mm; this was placed in tandem with the previously employed cylindrical magnet, resulting in a field of ~6800 Gauss at the tip of the pyramid. In every other respect, the next experiment was conducted identically to the preceding one with the cylindrical magnet, and the resulting images (all post-magnet vectoring) are shown in FIG. 5. The images on the left versus right are from neighboring slices, and the upper images are T2-weighted, whereas the lower images are T2*-weighted and more prone to distortion in the presence of these particles. By comparison of these T2*-weighted images to that on the bottom left of FIG. 4, we concluded that the use of the more focused magnet caused less undesired MNP localization to the normal tissues of the abdominal wall, while still achieving accumulation to the HEY tumor or peri-tumoral area.

EXAMPLE 11

Since the HEY tumor model demonstrated early, focal growth, and rapidly acquired significant size that should require angiogenesis, we reasoned that i.v. administration of MNPs, followed by magnetically-enhanced extravasation, would merit evaluation as an effective means of tumor delivery to a peritoneal tumor. We had not previously established the pharmacokinetic behavior of these MNPs, particularly in the plasma; therefore, it was uncertain whether, without purposely endowing the MNPs with "stealthing" components, they would survive endogenous clearance mechanisms (e.g., hepatic, splenic, renal) for a sufficiently long period of time to allow significant extravasation from the tumor vasculature. Nevertheless, using an identical protocol as for the previous experiment with the pyramid magnet, except that i.v. rather than i.p. administration was employed, we determined whether the current parameters of magnetic field strength and shape and MNPs might be effective. The results are shown in FIG. 6. The images on the left are pre-injection, and those on the right are following 2 hours of magnetic vectoring; as before, the upper images are T2-weighted, and the lower, T2*-weighted. Comparisons of the T2*-weighted images, pre-versus post-injection, are strongly indicative of tumor localization of the MNPs with this i.v. injection protocol. FIG. 7 shows the presence of magnetic nanoparticle aggregates and particles within the sections of the HEY tumors subjected to i.v. administration of MNPs.

Thus, the present invention is well-adapted to attain the objects and advantages mentioned, as well as those that are inherent therein. While numerous changes may be made by those skilled in the art, such changes are encompassed within the spirit of this invention as defined by the appended claims.

What is claimed is:

1. A method for delivering a therapeutic to target cells within a body, the method comprising the following steps:
preparing magnetically responsive therapeutic constructs comprising:
magnetically responsive carrier nanoparticles selected from the group consisting of: (a) single-domain nanoparticles comprising magnetite and having an average particle size ranging between 1 and 50 nanometers, (b) clusters of single-domain nanoparticles comprising magnetite, the particles having an average particle size ranging between 1 and 50 nanometers, the clusters having an average cluster ranging between 5 and 1000 nanometers, and mixtures of (a) and (b);
a silica coating encapsulating the single-domain nanoparticles;
a silane coupling agent bonded to the silica coating and having a specific pendant functional group comprises a carboxyl group capable of selectively binding with the therapeutic; and
the therapeutic chemically bonded to the silane coupling agent;
wherein the silane coupling agent comprises an alkoxysilylpropyl-O-polyethylene oxide urethane containing monomer units of polyethylene glycol (PEG) terminating in an alcohol function which has been oxidized to a carboxyl group;
introducing the magnetically responsive therapeutic constructs into the body; and
moving the therapeutic constructs to the target cell using a controllable magnetic field generator adapted to move the carrier nanoparticles in three dimensions.

2. The method of claim 1 wherein the magnetically responsive nanoparticles comprise superparamagnetic nanoparticles.

3. The method of claim 1 wherein the therapeutic comprises one or more hydroxyl groups.

4. The method of claim 1 wherein the therapeutic comprises a taxane.

5. The method of claim 4 wherein the taxane is selected from the group consisting of paclitaxel, docetaxel and mixtures of the same.

6. The method of claim 4 wherein the therapeutic comprises a taxane selected from paclitaxel, polyglutamic acid-paclitaxel, and polyglutamic acid-docetaxel.

7. The method of claim 1 wherein the therapeutic constructs are introduced to the body systemically.

8. The method of claim 7 wherein the therapeutic constructs are administered to the body intravenously.

9. The method of claim 1 wherein the therapeutic constructs are introduced to a tumor in the body via an intratumor arterial route.

10. The method of claim 1 further comprising delivering the therapeutic constructs through a membrane adjacent the target cells.

11. The method of claim 10 wherein the membrane comprises a tumor wall.

12. The method of claim 10 wherein the magnetic field generator is controlled to produce a repetitively-varying magnetic field gradient.

13. The method of claim 12 wherein the magnetic field intensity oscillates on and off.

14. The method of claim 12 wherein the magnetic field has an oscillating directional component.

15. The method of claim 14 wherein the oscillating directional component is perpendicular to a direction the therapeutic constructs are to be moved.

16. The method of claim 12 wherein the magnetic field generator comprises an electromagnet, the method further comprising controlling an electrical switch to oscillate power to the electromagnet.

17. The method of claim 12 herein the magnetic field generator comprises two pulsed electromagnets separated by a permanent magnet supplying at least about 50% of the magnetic field directed toward the target cells.

18. The method of claim 17 wherein the two electromagnets are directed parallel to the permanent magnet and wherein the controller is adapted to alternately pulse the electromagnets.

19. The method of claim 17 wherein the two electromagnets are directed at an angle relative to the permanent magnet direction and wherein the controller is adapted to alternately pulse the electromagnets.

20. The method of claim 12 wherein the magnetic field generator comprises three or more oscillating electromagnets surrounding and parallel to a permanent magnet supplying at least about 50% of the magnetic field.

21. The method of claim 1 wherein the therapeutic is bonded to the silane coupling agent through ester linkages, the method further comprising the step of using the controllable magnetic field generator to hold the therapeutic constructs proximate the target cells for at least the time necessary for the ester linkages to be degraded hydrolytically, in vivo and catalyzed by esterases, to release the therapeutic.

22. A method for treating cancer in a subject, comprising administering to a subject having cancer a therapeutic construct comprising:
    magnetically responsive nanoparticles selected from the group consisting of:
        (a) single-domain nanoparticles comprising magnetite and having an average particle size ranging between 1 and 50 nanometers,
        (b) clusters of single-domain nanoparticles comprising magnetite, the particles having an average particle size ranging between 1 and 50 nanometers, the clusters having an average cluster size ranging between 5 and 1000 nanometers, and
        mixtures of (a) and (b);
    a silica coating encapsulating the single-domain nanoparticles;
    a first silane coupling agent bonded to the silica coating and having a pendant carboxyl groups capable of selectively binding with a therapeutic;
    wherein the first silane coupling agent comprises an alkoxysilylpropyl-O-polyethylene oxide urethane containing monomer units of polyethylene glycol (PEG) terminating in an alcohol function which has been oxidized to a carbox group; and
    the therapeutic comprising a taxane selected from the group consisting of paclitaxel, docetaxel and mixtures of the same.

23. The method of claim 22 wherein the cancer is breast cancer, ovarian cancer, malignant melanoma, lung cancer, gastric cancer, prostate cancer, colon cancer, head and neck cancer, leukemia or Kaposi's sarcoma.

* * * * *